(12) United States Patent
Crews

(10) Patent No.: US 12,269,624 B2
(45) Date of Patent: Apr. 8, 2025

(54) SEALED FORCE VECTORING FLIGHT SYSTEM

(71) Applicant: Eric Jason Crews, Blacksburg, VA (US)

(72) Inventor: Eric Jason Crews, Blacksburg, VA (US)

( * ) Notice: Subject to any disclaimer, the term of this patent is extended or adjusted under 35 U.S.C. 154(b) by 438 days.

(21) Appl. No.: 18/045,294

(22) Filed: Oct. 10, 2022

(65) Prior Publication Data

US 2023/0127987 A1 Apr. 27, 2023

Related U.S. Application Data

(60) Provisional application No. 63/253,967, filed on Oct. 8, 2021.

(51) Int. Cl.

| | | |
|---|---|---|
| *B64U 20/87* | (2023.01) | |
| *A01H 1/02* | (2006.01) | |
| *B64C 39/02* | (2023.01) | |
| *B64D 1/16* | (2006.01) | |
| *B64D 27/24* | (2006.01) | |
| *B64U 20/60* | (2023.01) | |
| *B64U 30/00* | (2023.01) | |

(Continued)

(52) U.S. Cl.
CPC .............. *B64U 30/00* (2023.01); *A01H 1/027* (2021.01); *B64C 39/024* (2013.01); *B64D 1/16* (2013.01); *B64D 27/24* (2013.01); *B64U 20/60* (2023.01); *B64U 20/87* (2023.01); *B64U 50/19* (2023.01); *B60L 2200/10* (2013.01); *B64U 2101/40* (2023.01)

(58) Field of Classification Search
CPC ....... B64U 2101/40; B64D 1/16; A01H 1/027
See application file for complete search history.

(56) References Cited

U.S. PATENT DOCUMENTS 3,927,958 A * 12/1975 Quinn ...................... F23R 3/30
60/39.52
6,279,314 B1    8/2001 Valentian et al.
(Continued)

FOREIGN PATENT DOCUMENTS

CN    108088313 A  *  5/2018
CN    113320691 A  *  8/2021 ............. B64C 27/08
(Continued)

*Primary Examiner* — Christopher P Ellis
(74) *Attorney, Agent, or Firm* — Dunlap Bennett & Ludwig, PLLC

(57) ABSTRACT

An aerial craft and sealed force vectoring flight system is disclosed. The aerial craft includes a main body hull, lift jets, a generator, an electrical re-introduction circuit, a hydraulic pump, air flow compressors, an RPM sensor, a max speed limiter hydraulic draft by-pass valve, and a battery. The electrical re-introduction circuit throttles the generator into high-velocity rotation and yields excess electrical current to then be applied to the lift jets. The hydraulic pump pulls pressurized hydraulic fluid across a preceding hydraulic drive impellor such that the pressurized hydraulic fluid returns to confinement under pneumatic pressure faster than a discharge of hydraulic fluid. The air flow compressors generate electricity that is re-introduced into the lift electric motors. The RPM sensor and max speed limiter hydraulic draft by-pass valve speed regulate the generator. The battery initially powers the generator.

10 Claims, 3 Drawing Sheets

(51) Int. Cl.
  *B64U 50/19*   (2023.01)
  *B64U 101/40*   (2023.01)

(56) References Cited

U.S. PATENT DOCUMENTS

| | | |
|---|---|---|
| 6,357,171 B1 | 3/2002 | Harper |
| 7,753,314 B2 | 7/2010 | Nolan |
| 8,628,044 B2 | 1/2014 | Poulos |
| 8,720,205 B2 * | 5/2014 | Lugg ........................ F01D 5/03 60/767 |
| 9,796,487 B2 | 10/2017 | Yi et al. |
| 9,833,647 B2 | 12/2017 | Kawiecki |
| 9,938,024 B1 | 4/2018 | Fork |
| 9,976,514 B2 | 5/2018 | Rice |
| 10,577,133 B2 | 3/2020 | White, Jr. |
| 10,717,550 B1 * | 7/2020 | Zegler ..................... B64G 1/26 |
| 10,793,295 B2 | 10/2020 | Drexler |
| 10,815,015 B2 | 10/2020 | Drexler |
| 10,960,993 B2 | 3/2021 | Drexler |
| 11,821,367 B2 * | 11/2023 | Oqab ................... F02M 27/042 |
| 2008/0023587 A1 | 1/2008 | Head et al. |
| 2018/0064049 A1 * | 3/2018 | Cantrell ................... B64D 1/16 |
| 2018/0065749 A1 | 3/2018 | Cantrell et al. |
| 2020/0022312 A1 | 1/2020 | Gauvreau, Jr. |
| 2021/0329865 A1 * | 10/2021 | Norland ................ G05D 1/606 |
| 2022/0113029 A1 * | 4/2022 | Clift ......................... B64F 5/10 |
| 2023/0092645 A1 * | 3/2023 | Holmgren ............ C07D 303/04 435/157 |

FOREIGN PATENT DOCUMENTS

| | | | | |
|---|---|---|---|---|
| CN | 117016374 A | * | 11/2023 | |
| WO | WO-2018175552 A1 | * | 9/2018 | ............... A01G 2/00 |
| WO | WO-2023126936 A1 | * | 7/2023 | ............... A01G 7/04 |

* cited by examiner

SEALED FORCE VECTORING FLIGHT SYSTEM

CROSS-REFERENCE TO RELATED APPLICATION

This application claims the benefit of priority of U.S. provisional application No. 63/253,967, filed Oct. 8, 2021, the contents of which are herein incorporated by reference.

BACKGROUND OF THE INVENTION

The present invention relates a flight system able to be used in multiple ways to fight wildfires remotely, as a near-earth object mitigation tool, or to pollinate flowers.

Other systems in this type expel mass for propulsion in outer space. Current long-range asteroid mitigation are haphazard, cumbersome and/or are dangerous with very little precision where the total control of the effort is then a critical factor in a successful effort.

As can be seen, there is a need for a device and system as described herein.

SUMMARY OF THE INVENTION

In one aspect of the present invention, an aerial craft is disclosed that comprises: a main body hull; lift jets comprising lift electric motors; a generator comprising generator electric drive motors; an electrical re-introduction circuit that throttles the generator into high-velocity rotation and yields excess electrical current to then be applied to the lift jets; a hydraulic pump that pulls pressurized hydraulic fluid across a preceding hydraulic drive impellor such that the pressurized hydraulic fluid returns to confinement under pneumatic pressure faster than a discharge of hydraulic fluid; air flow compressors that generate electricity that is re-introduced into the lift electric motors; an RPM sensor and max speed limiter hydraulic draft by-pass valve to speed regulate the generator; and a battery for initially powering the generator.

As stated above, the flight system is able to be used in multiple ways to fight wildfires remotely, as a near-earth object mitigation tool, or to pollinate flowers. To fight wildfires remotely with active Nitrogen stratification upon the craft using air distillation to cause active collection of fire suppressant when in use also used attached to a net to redirect inbound asteroids correcting trajectory causing an impaction asteroid to then be safely redirected. The present invention provides a flight system with zero exhaust.

Wildfires using helicopter water drop can increase oxygen to a fire while producing a steam "draft" increasing airflow into the fire in two directions. As a wildfire suppression tool, it is a sealed flight mechanism with the ability to "harvest fire suppression mass as nitrogen while in use via on board air distillation These and other features, aspects and advantages of the present invention will become better understood with reference to the following drawings, description, and claims.

BRIEF DESCRIPTION OF THE DRAWINGS

The following figures are included to illustrate certain aspects of the present disclosure and should not be viewed as exclusive embodiments. The subject matter disclosed is capable of considerable modifications, alterations, combinations, and equivalents in form and function, without departing from the scope of this disclosure.

DETAILED DESCRIPTION OF THE INVENTION

Figures 1, 2:
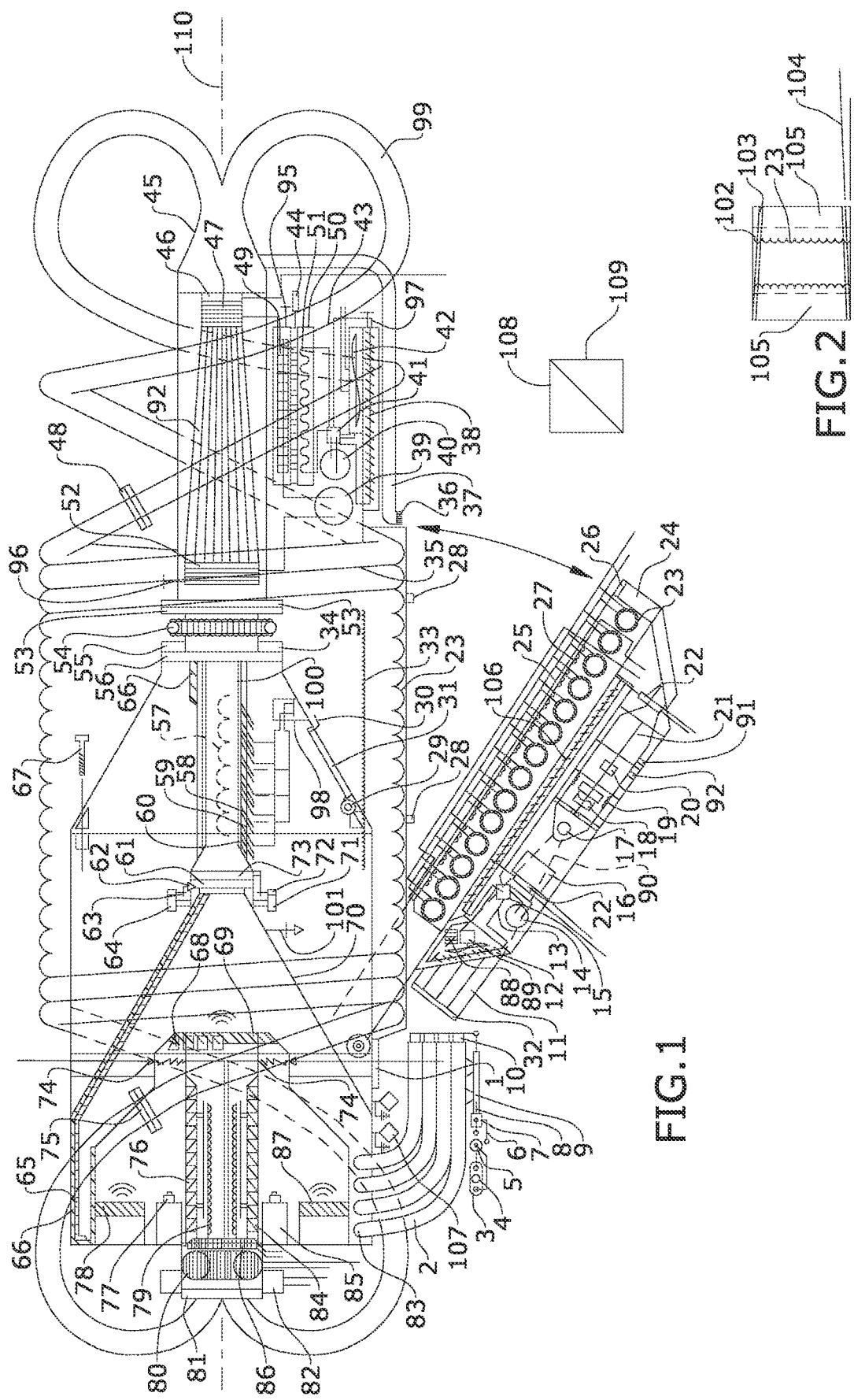
FIG. 1 is a schematic view of a cold plasma drive of the present invention.
FIG. 2 is a detailed view of a sealed force vectoring flight system of the present invention.

The subject disclosure is described with reference to the drawings, wherein like reference numerals are used to refer to like elements throughout. In the following description, for purposes of explanation, numerous specific details are set forth in order to provide a thorough understanding of the present disclosure such that one skilled in the art will be enabled to make and use the present invention. It may be evident, however, that the present disclosure may be practiced without some of these specific details. For the purpose of clarity, technical material that is known in the technical fields related to the present invention has not been described in detail so that the present invention is not unnecessarily obscured.

Figure 3:
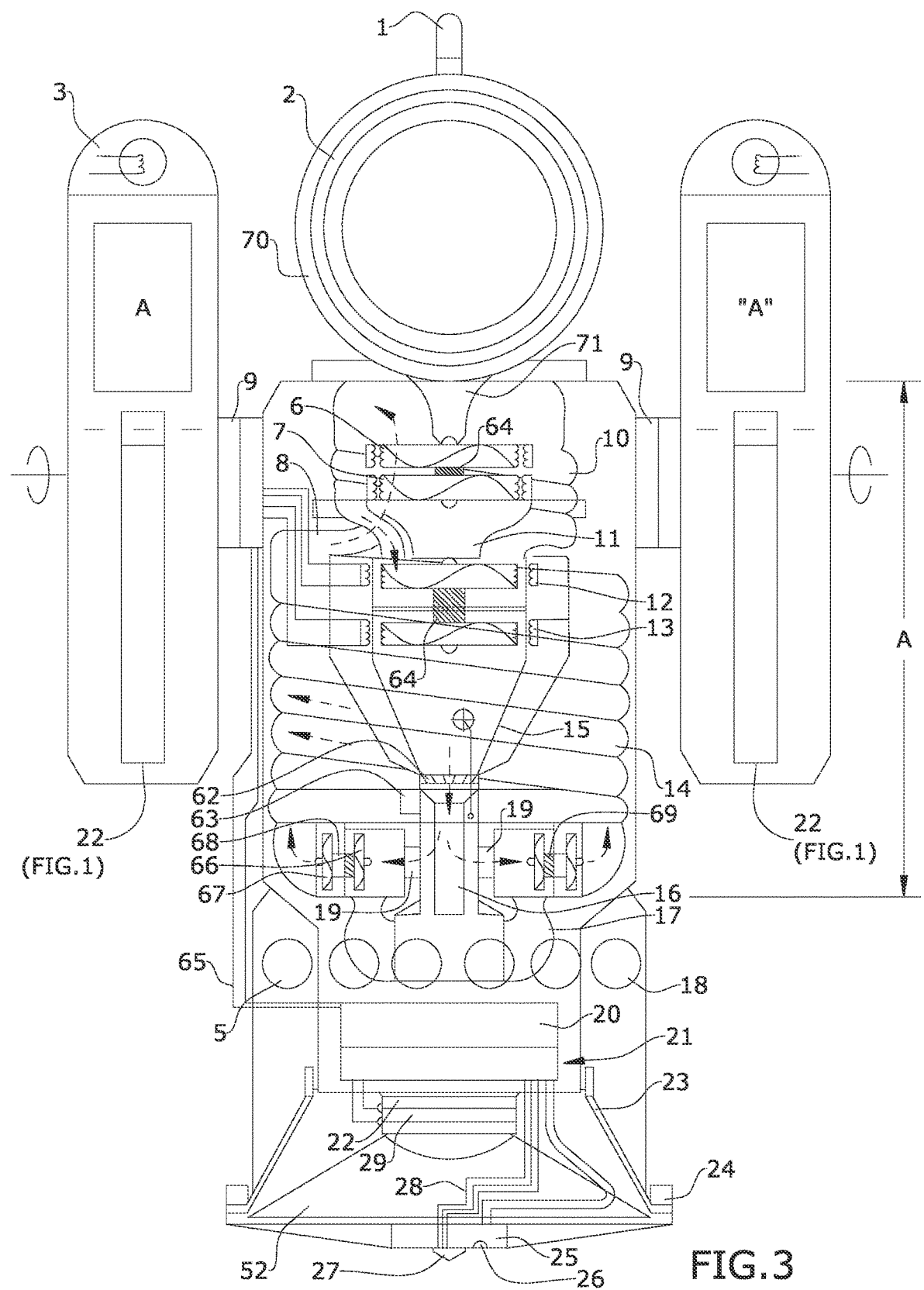
FIG. 3 is a schematic view of the sealed force vectoring flight system.
Figure 4:
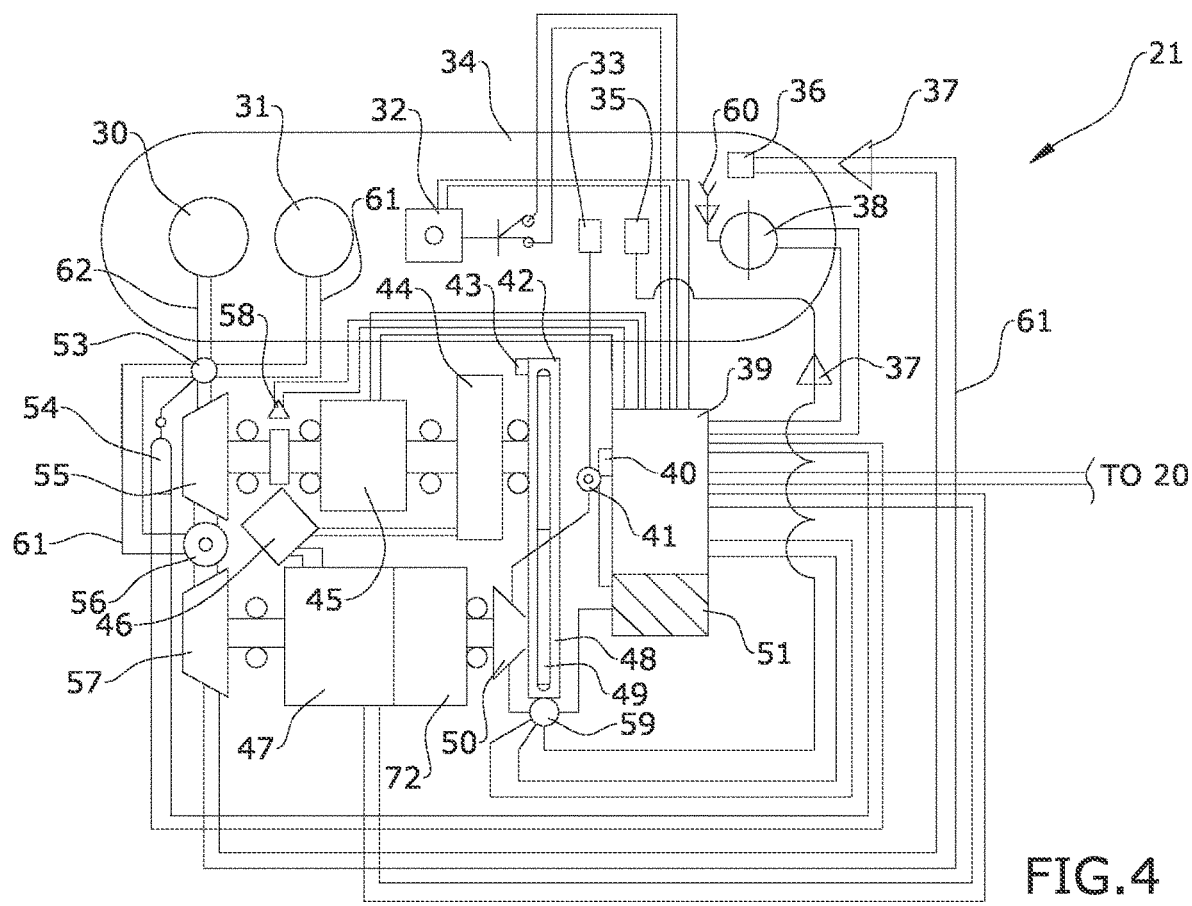
FIG. 4 is a schematic view of the drone power plant.

Referring now to FIGS. 3 and 4 a sonic automated pollinator (functioning as a "mechanical" bee) is disclosed. As discussed below, this device may also be functional as an asteroid mitigation tool. The following "sealed force vectoring" flight system operates upon a fuel-less platform using low-frequency audio pulse to pollinate crops in the field 24/7. Since the flight system does not cause physical discharge from the craft it can be used in outer space to then serve multiple functions such as asteroid mitigation and or to process metal in space to de-Gauss it.

Empty space contains electrical charge—a magnetization/ "Gauss effect" then occurs in metals contained within asteroids. This alters their orbital trajectories. Orbital trajectories then within the mapping catalogs must be updated to compensate for the gradual magnetic increase of induced magnetism and when solar flares or interstellar supernovae burst waves occur as they can carry magnetic "bubbles", then inducing magnetism within asteroids. Planetary magnetic fields, of solar system planets, are also a factor in the asteroid Gauss problem assessment.

The design of the present invention operates within a rf (radio frequency) "fence", to then stay in the boundaries of the crop in the field. When applied in environments, attempting the reversal of desertification, this design has a high-performance capacity compared to insect pollination.

The flora then requires a little assistance regarding pollination. This design, then in tandem with unlimited freshwater availability, can reverse the failed pollination situation, whereas introducing insect life to pollinate might not work well due to environmental conditions then being too stressful for the insect life. The system may accommodate a seed planting aperture (seeder), base docking, to then replant a forest or CO2 (Carbon Dioxide) sequestering scrub grass. When replanting forest, a center point rf (radio frequency), beacon would control the range of the craft, thus establishing the tree planting boundary.

PARTS LIST (OF FIGS. 3 AND 4)

1. red beacon lamp
2. white light "ring" shows both sides
3. lamp cover (different color lamps may indicate function)

4. vacuum producing electric "hyper jet"
5. audio speaker open port sum of 12 about 360 degrees
6. air flow impeller (input rotation to the ratio gear set driving the airflow compressor) and electric drive motor about the circumference of the air flow impeller
7. transonic air flow compressor and P.M. (permanent magnet Dc [direct current] electricity generator)
8. "air flow return "coil" injection tube—"pressurizes" the upper electric jet Letter "B's" air intake chamber
9. thru bore electrical current transfer "slip ring and lift/direction electric jet positional servo motor—allows the electric jet to rotate 360 degrees about the mounting axis while electrical current is then able to be transferred
10. upper air flow injection coil/tube—intake air flow coil to letter "C"
11. air chamber—intake air flow chamber to letter "B"
12. main electric lift jet air flow compressor and electricity generator about the circumference
13. main electric lift jet air flow impeller (input rotational torque to the ratio gear set containing a revolutions per minute (RPM) sensor to then "govern" the rate/speed of the lift jet adjusting altitude)
14. main force static "nullification" air flow "return coil"/tube
15. main lift electric jet venturi "funnel" causes higher air flow exhaust pressure
16. venturi airflow diffuser open port tube allowing low-pressure effect in the chamber being causes by the sum of four vacuum producing hyper electric jets 4 at quadrant points about 360 degrees from the top view center point
17. vacuum jet intake manifold (upon each vacuum jet)
18. screened air port (hole bore) allows the audio speaker to cause percussion correctly
19. funnel venturi diffuser horizontal vacuum jet intake tube
20. avionics/flight logic electronics/communications electronics/refrigeration evaporator
21. hyper drafting fuel less generator "bay"/refrigeration evaporator
22. audio speaker magnet (audio speaker coil assembly)
23. audio speaker mounting system sum of 12 about 360 degrees
24. audio speaker mounting system sum of 12 about 360 degrees
25. infrared camera and visual camera information unit—allows the detection "location" of the flowers to be pollinated by the percussion of the audio speaker using low tone
26. infrared camera/altimeter sensor
27. visual camera/lamp and air pressure discharge port, air pressure extrapolated from the generator system's air compression cycle
28. air pressure hose
29. audio speaker magnet
30. oil drain (base of the dual component pressure tank)
31. oil drain (base of the dual component pressure tank)
32. pneumatic over pressure safety valve (vents to the exterior) and pneumatic pressure sensor (electric) that communicates with the logic processing "system mapping" electronics to switch the "start" air impeller to the air compressor function via valve number 41 then being automatically adjusted
33. pneumatic "tank top mount" air compression fitting
34. dual component air pressure and oil "hydraulic fluid" pressure tank air pressure causes oil pressure
35. pneumatic "tank top mount" air compression fitting
36. hydraulic fluid (top mount) oil—"silicon oil"/hydraulic fluid "oil return" compression fitting
37. one way valve
38. oil fill and oil level "send" (detects the level of oil within the dual component pressure storage tank)
39. generator system logic processor/electricity management control/electronic sensor processing/relay and fuse "block"
40. inductance control—control dissipation of induced static electricity—motion of fluid even non-electrically conductive hydraulic oil can induce electrical charge building capacitance. This unit then control dissipates the unwanted electrical charge for safe system operation . . . an "artificial electrical ground". The system mounting frame/bracket is then the electrical ground "electrically connected" to the static electricity dissipation unit also controlling the dissipation of unwanted magnetic inductance to prevent an electrical shock hazard.
41. air flow direction electric position valve—natural position closed opens to "start the generator" closes while the generator is in the "run" mode and positions to "re-fill" the operating pneumatic pressure within the dual component pressure storage tank number 34
42. oil retainer encasement drive chain and sprocket system sealed lubrication encasement—non-flammable lubrication/non electrically conductive lubrication
43. oil fill port/top casing plug
44. electricity generator
45. dual shaft electric drive motor
46. voltage regulator output electrical current electrifies induces the field coil of the main electricity generator number 47
47. main electricity generator
48. large sprocket
49. small sprocket
50. dual function air compressor/air "start" impeller
51. air intake and or air exhaust filter "box" and air filter
52. audio speaker external exposed surface then of material atop the actual speaker to then retain airborne pollen. A looped fiber mesh will then retain the pollen also by slight magnetic tilt in the material.

53. dual valve unit system speed adjustment valve—electric positioning valve via solenoid system

54. electric valve solenoid

55. hydraulic fluid impeller "fluid draft impeller" causes system speed advancement via fluid suction incurred by the high-speed hydraulic pump, number 57 rotating faster than the impeller caused by the system ratio gear set, number 72, and the drive chain and sprocket system within the oil lubrication encasement

56. divergence valve/system speed safety "speed limiter valve" allows the dampener valve to open under high suction for flow pipe structural integrity and allows for fluid pressure to "by-pass" the hydraulic draft impeller causing stable "system run speed" used in tandem with the electric "re-introduction circuit electric "throttle" circuit

57. high-speed hydraulic pump

58. hall effect R.P.M. (revolutions per minute sensor) used to regulate the system electrical "re-introduction" circuit to increase the total speed of the generator producing higher levels of available output electricity. i.e. "a percentile of generated electricity" is then able to be "re-introduced" to the generator's drive line's electric motor to increase the generator's electricity output level.
59. multi position electric valve changes the air flow direction for the air impeller, number 50, to allow air pressure from the dual component pressure storage tank to cause system "Start rotation" or to then change direction causing the air impeller to act as an air compressor then "re-filling" the dual component pressure storage tank, number 34, with air pressure also directional compression fitting for the air discharge pressure line to the pollinator tip (air pressure discharge tip) upon number 27.
60. pneumatic one way "fill valve" cause the air pressure within the dual component pressure storage tank, number 34, to then be "set" at the system's "operating pneumatic pressure level"
61. oil flow pipe
62. venturi shutter "throttle" valve

63. electric "throttle valve/shutter valve" electric position electric motor and mechanical linkage system

64. electric jet ratio gear set system (contains R.P.M. sensors that report to the avionics) aligned so that the high side of the 1:10 ratio is then causing higher airflow compressor speed

65. ribbon wire multi wire/communications wire—communicates with the lift jet and positional servo to control the flight of the unit

66. air flow compressor circumference electric motor

67. air flow impeller circumference electric motor

68. dynamo

69. electric jet ratio gear set system (contains R.P.M. sensors that report to the avionics) aligned so that the high side of the 1:10 ratio is then causing higher airflow compressor speed

70. counterweight balance ring to allow for a "balanced" tilt when the unit is directing the audio speaker toward the flower to be pollinated

71. airflow guide

72. 1:2 sealed lubrication ratio gear set—high side rotation union tandem with the oil pumps internal "pump wheel"

DESCRIPTION

The above-listed components are arranged and coupled together as shown in FIGS. 3-4 and described herein.

The above design system is intended to then be able to operate in environments where natural or manual pollination becomes too involved. The design is a high-speed device that is able to "re-introduce" produced electricity back into the system electric motors both for the electric lift jets that cause closed cycle propulsion (sealed force vectoring) and to the generator's electric drive motors to produce ample excess electrical current for lighting/avionics/audio pulse systems/radio frequency systems—navigation and flight position systems.

The design's generator system is a "pressurized hydraulic draft accelerator" using an electrical re-introduction circuit to "throttle" the power generator into high-velocity rotation yielding excess electrical current to then be applied to the craft's sealed lift engine systems. Hydraulic fluid does not stretch in the confinement of a rigid flow pipe so when the hydraulic pump is "pulling" fluid across a preceding hydraulic drive impeller the pressurized oil then returns to confinement under pneumatic pressure faster than the discharge of hydraulic fluid (electrically non-conductive and non-flammable hydraulic oil). The air flow compressors also then generate electricity about their circumference generator also able to be re-introduced into the electric jets electric drive electric motors.

The generator system 21, then speed regulated by R.P.M. sensor and by max speed limiter hydraulic draft by-pass valve 56. The "operating pneumatic pressure in the dual component (hydraulic fluid and air pressure) pressure tank 34, then of sufficient air pressure to then counteract upon/nullify the electromagnetic resistance of the generators traversing magnetic fields, the mechanical resistance encountered within the ratio gear set and the drive chain and sprocket system. Air pressure in the said pressure storage tank causes oil pressure acting then like a large compression "piston" as the exposed surface area of the oil is exposed to the air pressure.

The generator system 21, then used for outer space functioning, is then mounted upon a centrifuge to maintain fluid location, (circumference), for system "Start" the centrifuge is then driven by electric motor and electrified by a battery. For outer space functioning, the generator system 21, is then also double encased with the outer encasement acting as a gas capture cycle to then allow the dual component pressure storage tank to discharge into encased lower pressure also able then to allow the generator system to pull gas pressure from the outer encasement re-pressurizing the dual component pressure storage tank used in number 21.

The system's audio speaker then also acts as a pollen collector upon its exposed surface so that when the low tone audio pulse is instigated a cloud of pollen is then ejected in front of the air displacement nozzle 27 then directing the pollen to the flower. The infrared and visual cameras assist in avionics flight positional systems and detection of the flower to then cause the designs function sequencing. In other words, the drone finds the flower tilts the speaker (audio pulse), and initiates air discharge to then pollinate the flower. This sequence repeats upon the next flower is detected.

Since the design can operate 24/7, the number of plants pollinated in a given time frame is then at a higher rate. With the current bee colony collapse disorder occurring, stabilization of pollination for fruits and vegetables is critical. A safety system for food pollination assists in solving global hunger.

The design coil "return" airflow "Argon"—an inert Nobel Gas, coil manifolds then "off-set" the reactant force in the force equation by reintroducing the airflow at 90 degrees nullifying the static in the force equation allowing constant high pressure then "injected" into a vacuum.

The generator system 21 and infrared camera and visual camera information unit 25 are then connected together with dual video communication wiring and additional electrical power feed wires.

It should be noted that the "designs" scale then of variable size 10" (inches) tall thru 10'+ (feet) tall. The larger size then fitted with an additional cold plasma toroid compression engine system, listed at: https://www.designdeskinc.com/cold-plasma-drive-toroid-static-compressor.html as of the filing date of the present invention and described with respect to FIGS. 1-2, to then serve as a N.E.O. (Near Earth Object/asteroid impact mitigation), a mitigation tool driven remotely.

The long-range engine additions then mounted upon the servo-mounted electric jets so that they would then be in addition to the sealed force vectoring electric hyper jets letter "A". The asteroid capture net then locked to the craft hull upon the "open hoop" (open bore of the lamp ring 2).

The "hoop" then used to lock a heated net of large diameter to mitigate inbound asteroids remotely.

A "Near Earth Object Mitigation tool" then about the circumference of the net with multiple craft at equal distant degrees. Triangular nets then would be tethered at the apex of the net. The net may be an electric tether wench and reel connected to the hull to allow for greater effective distance to control large asteroids. The present invention always approaches or "captures" asteroids by netting them from behind. This allows for controlled pressurization of the net system and gradual trajectory correction using the sealed force vectoring pneumatic thrust system within the "mechanical bee".

This system reduces the total cost of mitigation and allows the travel speed/response time, of the mitigation method to then be responsive in a timely fashion due to the rate of travel of the cold plasma drive. Lifting large nets will implement multiple craft about the circumference of the heated net. The speaker then a communications antenna transmitter/receiver system allows the operator to then control/drive the N.E.O. correction remotely. It is noted that beacon lamp 1, then hinge mounted to "recess" into the ring housing when then craft is in mitigation function.

The following paragraphs are a few further notes regarding the above-described system.

A proximity sensor system is then onboard detecting other units of the same type to then prevent accidents mid-air collision when multiple units are applied over one field.

This system may be adapted to then act as a remote wildfire suppression system then using the active reduction of Nitrogen (air distillation), used as a fire suppressant directly from the surrounding air using a small cost-effective unit to then distill air for "active" fire suppressant harvest upon the unit.

This system may be useful in litter clean up if equipped with low pressure hydraulic grappling. One compressor lever upon the front one compressor lever upon the back of the unit with slight lift shock absorption upon the mounting assembly (manual operator required). This avoids human disease from being incurred to the clean-up crews if contamination (radiation) or pathogen is then in the refuse.

The design may also be adapted to then be used in a similar fashion for solar gain reduction then in a similar manner to the solar radiation diffuser satellite listed at https://www.designdeskinc.com/solar-radiation-diffuser-satellite.html as of the filing date of the present invention. The speaker system then the location of the diffuser's incident cone transmitter and electron injection system. This may be a smaller more cost-effective method to then reduce the total solar gain (watt per meter) to control global warming by reducing/compensating for the pollution particles falling out of the atmosphere when switching to clean energy systems. An "electric umbrella" transmitting electrons upon a carrier wave in the shape of a cone, toward the Sun, to shield the total planet from a singular object. Multiple craft then in redundant function may be required. The design then not to cause unwanted magnetic "Gauss" of asteroids upon the opposite side of the Sun.

The craft may be use for agricultural irrigation as an alternative to expensive center pivot irrigation. Either in a similar fashion to center pivot where the topography is inclined allowing for viable land to be utilized that would otherwise be to difficult to irrigate. The hose then clamped thru the "open ring" to dispense water along the length of connected units operating in tandem. The design also then could be used for radio tag location of plants . . . single water dump flying independently.

Depending upon scale and function the refrigeration of the avionics and electricity management control then may be required. The refrigeration condenser is placed within the open ports at number 18, as a "ring" condenser with the refrigeration evaporator then within the electronics "bay" cooling both number 20 and number 21. The cooling "effect" is then able to transfer to the system venturi via the internal frame structural members that are thermally insulated. This aids in keeping the circumference windings upon the main engine system wire windings and magnets cool.

Sealed flight vessel a mechanical balloon causing return air flow to offset the static in the force equation to nullify the force static maintaining pressure (argon) displacement a greater force than craft weight upon a hydraulic draft accelerator electrical generator to maintain correct safe operation then shielded within an inductance cage.

The design will break Earth's gravity and be able to travel at high speed with the design powered by hydraulic draft accelerator electrical generators to net asteroids and change an inbound or impactor asteroid. The main body "hull" then acting as a mechanical balloon maintaining high gas pressure within it's chamber the force vectoring the gas into mechanically produced vacuum to cause sealed lift. The vector change the attained by electric servo positioned motors also with the cold plasma drive (discussed in greater detail with respect to FIGS. 1-2) mounted upon the 360 degrees side mount servomotor systems. As shown in FIG. 3, the cold plasma drive's placement location is denoted by the FIG. 1 notations in parentheses. Multiple unit then in tandem will lift a net into outer space and capture an asteroid from behind to control its vector.

In an exemplary embodiment, the present invention may be made as described above, shown in the figures, and as follows. Injection molding minimal raw tooling may be used to produce the system. The electronic system may be produced upon repairable circuit boards.

As discussed above, the flight system tool has many functions can be adapted to serve many applications: mechanical bee, wildfire suppression system flight drone, agriculture, and as an asteroid mitigation tool. Many functions can be adapted to the base flight frame "body". In other exemplary embodiments, the mechanical pollination of food "audio speaker model" will have the ability to inter change components to mount a wild fire suppression system using the active harvest of atmospheric Nitrogen to displace the oxygen fueling wild fires. The "audio speaker bay" then also may accommodate an electron transmitter and microwave transmitter to shade the total planet if used in multiple numbers to drop the total Solar thermal gain reducing Global Warming due to CO2.

Making reference, now, to FIGS. 1-2, a cold plasma drive "toroid static compressor" is disclosed. The following aerospace engine design system is then intended to assist in asteroid mitigation as the speed that is attainable to then respond within a timely fashion is then present with this design system.

The system uses particle accelerators upon a "swing arm" to then cause magnetic field to accelerate the cold plasma then laden with random electron to then be directed by toroid electromagnetic who's magnetic field is then compressed by microwave radio transmitter causing the electron and inert noble gas to excite in velocity causing an effect of high pressure upon one end of the engine system and low pressure upon "within" the aft of the engine.

The electron absorption system then aids in the low-pressure effect. The low inert gas pressure level allows for high engine speed. The system will also work while retaining vacuum. The design system then electrified by fuel-less electricity generator. The system uses a "super cooler" refrigeration system to then also chill the interior of the electrically insulated hull.

The design is a radio (microwave) compression system that also uses the injection of electrons as the discharge rate then can keep pace with the required pressure system "feed rate". The venturi acts like a passive compression system increasing pressure and speed of the cold plasma. The "swing arm" containing particle accelerator cylinders then acts like pumps within the helical coil. The act of perpendicular reintroduction of working mass, then off sets the "static" in the force equation. Potential power sources for the system are listed at https://www.designdeskinc.com/exciter-delta-type.html or https://www.designdeskinc.com/automotive-vacuum-drive-accelerator.html (as of the filing date of the present invention).

The system uses two toroid electromagnetic doughnuts also permanent magnets with the magnetic field then compressed by radio transmitter (microwave transmitter) to then peel the field causing a compression bubble that contains loose electrons. The linear particle accelerator then causing directional force to pump the plasma toward the compression venturi. Care must be taken not to cause resonance within the compression sequence as not to weaken the confinement material.

PARTS LIST OF FIGS. 1 AND 2

1. Electron injector and linear cold plasma accelerator (particle accelerator/electromagnet field compressor) mounting brace sum of eight about 360 degrees
2. cold plasma return manifold "insulated" (thermal and electrically)
3. hydraulic fluid reservoir
4. pressure rated hydraulic fluid reservoir screw threaded pressure cap
5. electric hydraulic fluid pump
6. hydraulic fluid pressure lever (opens the "swing arm" and by the fluid pressure hinge allows the swing arm to then be positioned in the "open" position then to be serviced if required)
7. hydraulic fluid pressure valve gates
8. piston bleed valve
9. hydraulic piston extends the cold plasma return tubes to seal the cold cycle return when the swing arm is then compressed into the recess
10. telescoping extending return tubes (encased in thermal cover that is also electrically non-conductive)
11. cold plasma return tubes
12. refrigeration condenser
13. refrigeration flow switch box
14. electric refrigeration compressor
15. electrical ground location point
16. system electronics control panel and system circuit path control electronics (fault and circuits display panel)
17. compound jet (cold plasma pump) discharge port (both into the super coolers evaporator and into the return manifold, number 90). The evaporator cold temperature cycle then re-introduced into the cold plasma return tubes 11 with a valve system to then inject (at 90 degrees) the "cold return" flow into the main engine system. The helical particle accelerator coils are also cooled by this cycle to prevent the particle accelerator wire from overheating. The pressure produced from the compound electric jet in the swing arm force pressurized the cold air flow. This aids in cooling of the particle accelerator. This also augments the low-pressure effect in the aft of the engine system.
18. pneumatic impeller
19. electric dynamo/electric motor (brush less)
20. 1:20 ratio gear set high side rotation tandem with number 21 "pneumatic compressor"/DC (direct current), generator—dynamo
21. pneumatic compressor/electricity generator brush less
22. Swing arm"—"locking hydraulic compressor" compresses the "swing arm" into the recess piston rod end inserts into locking hoops 28 (described below)—sum of four top and bottom of the swing arm . . . also hard lock bolts upon mechanical screw adjusting hinges as part of the system to hard clamp at specified torque setting to then hard lock the swing arm into place for operation. This is so that the swing arm is aligned correctly into the recess. The hinge then able to travel to and from the center line point by mechanical screw crank with locking mechanism for component exchange/repair.
23. cylinder plasma accelerator (particle accelerator)
24. compression gasket (high thermal tolerance dynamic temperature range high/low parameter)
25. gasket
26. cold plasma return bore
27. "Swing arm" locking "electro-magnetics" (attractant to the main engine housing casing),—causes the swing arm to "lock". The swing arm pivot hinge then has a sliding tower to allow for correct alignment and "compression" bringing the swing arm parallel before final hydraulic piston compression causing the cylinder particle accelerators to become sealed. The swing arm pivot then is moved by ratchet compression screw thread bolts, a manual function that requires a specific torque setting. The "swing arm" then also with right angle post particle accelerator closes to the pivot hinge to then close correctly (depicted in the "opened" position). This allows for continuity of the coil helix then able to complete a pressurized flow cycle back to the system intake.
28. "Swing arm" locking hoops
29. maintenance access door hinge
30. access door handle
31. access door
32. gasket
33. engine casing "locking" electro-magnetics
34. high frequency microwave transmitter
35. cold plasma "return" coil (two pieces top and bottom) off sets the static return in the force equation by perpendicular flow of plasma
36. high low temperature cold plasma gasket
37. cold plasma flow pipe (causes low pressure/negative pressure effect in the aft venturi, number 45)
38. super cooler refrigeration condenser
39. electric pump super cooler refrigeration fluid pump for the cooling exchanger (heat exchange pump)
40. electric compressor super cooler refrigeration compressor
41. super cooler refrigeration switching (refrigeration control unit—electric valve)
42. super cooler refrigeration condenser cooler fan and electric drive motor assembly
43. super cooler cold box—insulated
44. super cooler louver slide valve—allows the exchange of temperature at specified interval according to the size of port/position of the louver 45. aft venturi "funnel"
46. electron absorption aft assembly "ring"
47. aft cooling ring contains cycling cold fluid
48. union plates (bolt nut, and gasket assembly)
49. cooling exchanger contains temperature transference fluid
50. louver gate valve
51. refrigeration evaporator
52. aft cold ring cycles cold fluid to number 47 keeping the electron absorption collector cool
53. bolt plates/union plates bolt, nut and gasket assembly
54. electromagnet toroid (causes "dough-nut" shaped electromagnetic field that is then compressed perpendicular by the adjacent microwave transmitter, number 55) current level sensor unit also measures electrical gain incurred by permeation and or internal gain to adjust the electron injection rate or to control decompress the internal flow cycle. The unit is connected to engine system electronic circuit logic control, which is a critical safety feature.
55. micro wave transmitter
56. union bolt plates—contains nut bolt and gasket assembly
57. magnetic field in the forward electron absorption assembly
58. permanent magnets coil wound with wire to cause electromagnets that have one pole of the electromagnet magnetically sealed to then cause the produced magnetic field by the adjacent electromagnet to then direct the cold plasma electron to then be induced into the inductance "pick up", number 100 for redirection into the system.
59. inductance balancer "controls" the stray voltage to "de-energize" electrically any unwanted incurred electricity in the electron absorption system between the "sealed" end of the permanent magnets
60. electromagnet/wound permanent magnet (one pole sealed)
61. shutter valve "throttle gates" allows for variable "pressure" discharge
62. throttle shutter valve drive gear
63. throttle valve "throttle gates" drive gears
64. "throttle valve" drive electric motors (may be assisted by hydraulic fluid pressure with hydraulic impeller system tandem operating with the armature of the electric motor number 64)
65. radio frequency insulator
66. electrical insulator
67. bolt nut and gasket assembly (from center point of engine system polar array sum of 24 bolts and nut about 360 degrees)
68. electron discharge ports
69. main radio microwave transmitter doughnut "ring" transmitter
70. force compression venturi "funnel" (internal microwave and temperature insulated venturi)
71. "throttle valve" drive electric motors (may be assisted by hydraulic fluid pressure with hydraulic impeller system tandem operating with the armature of the electric motor number 64)
72. transfer gear
73. shutter valve plates sum of two counter-rotating plates allows for different pressure level discharge
74. electric arc node ring (sum of 12 about 360 degrees total sets +/−)
75. bolt, nut and gasket bolt plate assembly
76. electromagnetic "bottle" electromagnetic confinement—discharge allowed in one direction into the venturi
77. electron emitter
78. microwave transmitter and particle accelerator control electronics—(power management "bay")
79. linear particle accelerator
80. toroid electromagnetic doughnut (produces doughnut-shaped magnetic field that is perpendicularly compressed by the microwave radio transmitter number 82)—assist in cold plasma focus
81. cold plasma reintroduction—coil return mounting plate
82. microwave radio transmitter electronica and internal vacuum system—vacuum system external argon flow pipe system to and from argon storage pressure tanks
83. cold plasma return ports (sum of four each side)
84. electromagnetic bottle insulation (magnetic fields insulator)
85. electron emitter
86. inductance "pick up" electricity collector—has the ability to "re-direct" induced electrical flow safely also keeping the engine casing from induced electricity—encased
87. radio microwave transmitter
88. vent allows engine room air to traverse across the refrigeration condenser to cool the refrigeration condenser
89. refrigeration condenser blower fan and electric motor assembly
90. lower cold plasma discharge manifold
91. one way fill valves inert noble gas fills the engine or can by electric exhaust valve store the inert noble gas to then "run" the system in "vacuum mode" function contains additional gas (argon) pumps "to and from" gas storage pressure tanks. The pumps and pressure storage tanks are electrically grounded and electrically insulated.
92. chilled electron absorption cone multiple electron ribs
93. open center orifice (center of the throttle valve is an open orifice—in effort to reduce accidental venturi over pressurization grants a lag time for the system to automatically adjust—information attained by the system electronics sensors.
94. aft venturi pressure sensor
95. temperature sensor
96. temperature sensor
97. temperature sensor—thermostat—actuates the blower fan
98. electron absorption discharge receptacle
99. cold plasma return helix pipe (temperature insulated—electrically insulated and electrically grounded outer casing) the entire helix return tube is a particle accelerator to then guide the flow of electron preventing the inner surface for damaging the interior walls of the tube. The system will "guide" the electron toward the center of the tube. The thrust then from the swing arm as well, different levels of acceleration.
100. inductance tube electrical "pick up" causes low-pressure effect post high pressure discharge—stainless steel composition—"recycles" electrical current back into the engine design's components safely i.e . . . feeds current to the particle accelerators, super cooler engine cooling system, the electron injection system, focus toroid magnetics, linear particle accelerator, magnetic confinement "bottle", electromagnetic lock system, arc node system and the radio (microwave transmitter system). The system will also contain an electricity "dump"/"discharge" control system to de-energize critical components if and when it becomes required as a safety feature function!!! This also acts to control engine internal unwanted electrical gain affecting system safe pressure levels.

101. venturi pressure, electrical current level sensor and temperature sensor
102. taper angle (for compression fit)
103. gasket
104. compression angle
105. refrigerated chamber
106. refrigeration evaporator
107. plasma box system artificial electrical ground to prevent any unwanted electric shock hazard
108. system de-energization unit—connects to all electrical components to drain the engine of electricity automatically regulates max system electrical "pressure
109. instrumentation logic electronic logic circuits control unit engine control panel.
110. mirror line to indicate the same parts/components upon both sides of the line upon the cold plasma drive.

DESCRIPTION

The above-listed components are arranged and coupled together as shown in FIGS. 1-2 and described herein.

Additionally, the system final encasement (system cover) then composed of a lead particle (atomic number 82) and a titanium particle (atomic number 22) embedded in carbon graphite laminate composite of carbon strand fiber and high-temperature epoxy (serving as gamma radiation shielding).

The laminate cured with epoxy in an enclave (the system control panel the insulated as well and system electronic/circuit control will also dock to "ribbon wire" bus clip to then be able to be controlled from the ship's helm. Where required within the system high temperature ceramics are then used for insulators and mounting arc node points. Ceramics then also used in the electron emitter guide system.

The engine system described with respect to FIGS. 1-2 may be used as described at https://www.designdeskinc.com/theta-class-interceptor-asteroid-mitigation.html (as of the filing date of the present invention).

It is noted that the sub-atomic "Quark" then being affected at high velocity a critical phenom to observe within the engine system as time is a factor/"rate of travel", also energy in the bond (strong force weak force atomic covalent "static" factoring, Muon, Tachyon, Neutrino, etc.). Particles in outer space that permeate mass are a mass gain factor within the engine affecting engine control.

It is further noted that engine temperature is then maintained by the cooling system with the transonic hyper electric jet engine then compressing the plasma into the exhaust venturi allowing a measured level of flow "pressure" to enter the super cooler sealed refrigeration evaporation "chamber" whose exhaust is then valve regulated with pressure safety dump valve and adjustable regulation valve to number 11's recess, allowing the total engine system flow to chill. The chiller fittings then reside in the tube containing the extending flow pipes so that when fully recessed the fittings still allow chilled plasma flow.

The particle accelerator "return coil" is then able to be made to "stretch" the acceleration "mass" then causing a cooling effect in addition to the swing arm mount refrigeration system.

When traveling at high velocity "inducing" electrically from the electrical charge of empty space is also a biomedical factor to prepare for, i.e., the "effects" upon the physical body. Brains are electric—don't over-induce electrically.

It is also noted that the engine design can be operated void of inert Argon, i.e., the internal vacuum with only microwave transmission and excited electron.

The electric jet system then powered by the fuel less hydraulic draft accelerator while generating electricity to increase the electric jet's input electrical current level. This increases the hyper jets and vacuum hyper jets total speed to attain sealed force vectoring. The design maintains a pressure bubble within the main engine chamber then injecting air (Argon) pressure into vacuum causing lift.

In an exemplary method, the present invention may be used as follows. A flight operator instigates generator spin-up mounted upon a centrifuge to cause hydraulic fluid in the correct location. The design, electrified by the hydraulic draft effect" generator system, electrifies the mechanical balloon system spinning up the internal propellers that compound velocity and rate also generating higher ranges of electrical current. The communication to the craft then by encrypted radio remote control. The high-speed cold plasma drive (FIGS. 1-2) the instigated when the mechanical balloon system has reached outer space once the servos have been "programmed to vector to the asteroid to be redirected. The asteroid is captured from behind with multiple "Mechanical Bee" using a heated capture net. The "Mechanical Bees" the safely redirect the asteroid.

While one or more preferred embodiments are disclosed, many other implementations will occur to one of ordinary skill in the art and are all within the scope of the invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. Other arrangements, methods, modifications, and substitutions by one of ordinary skill in the art are therefore also considered to be within the scope of the present invention, which is not to be limited except by the claims that follow.

The use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

What is claimed is:

1. An aerial craft comprising:
   a main body hull;
   lift jets comprising lift electric motors;
   a generator comprising generator electric drive motors;
   an electrical re-introduction circuit that throttles the generator into high-velocity rotation and yields excess electrical current to then be applied to the lift jets;
   a hydraulic pump that pulls pressurized hydraulic fluid across a preceding hydraulic drive impellor such that the pressurized hydraulic fluid returns to confinement under pneumatic pressure faster than a discharge of hydraulic fluid;
   air flow compressors that generate electricity that is re-introduced into the lift electric motors;
   an RPM sensor and a max speed limiter hydraulic draft by-pass valve to speed regulate the generator; and a battery for initially powering the generator.

2. The aerial craft of claim 1, further comprising an audio speaker.

3. The aerial craft of claim 2, wherein the audio speaker is configured to collect pollen.

4. The aerial craft of claim 3, further comprising an air displacement nozzle configured to direct the pollen to a flower.

5. The aerial craft of claim 1, further comprising an infrared camera.

6. The aerial camera of claim 5, further comprising a visual camera.

7. The aerial craft of claim 1, wherein the generator is mounted on a centrifuge.

8. The aerial craft of claim 1, further comprising a ring for coupling with a net.

9. The aerial craft of claim 1, further comprising argon within the main body hull, the argon causing lift.

10. The aerial craft of claim 1, further comprising a cold plasma drive.

* * * * *